(12) United States Patent
Wedekamp

(10) Patent No.: US 6,642,527 B2
(45) Date of Patent: Nov. 4, 2003

(54) UV RADIATION DEVICE FOR TREATING FLUIDS WITH A SIMPLIFIED RADIATION CHAMBER

(75) Inventor: Horst Wedekamp, Herford (DE)

(73) Assignee: Wedeco AG Water Technology (DE)

( * ) Notice: Subject to any disclaimer, the term of this patent is extended or adjusted under 35 U.S.C. 154(b) by 0 days.

(21) Appl. No.: 10/173,964

(22) Filed: Jun. 18, 2002

(65) Prior Publication Data

US 2003/0010927 A1 Jan. 16, 2003

(30) Foreign Application Priority Data

Jun. 19, 2001 (DE) .......................... 101 29 178

(51) Int. Cl.$^7$ ........................... A61L 2/10; G01N 21/01; C02F 1/48; B01J 19/08; B01J 19/12
(52) U.S. Cl. .................. 250/436; 250/428; 250/432 R; 210/748; 422/186.3
(58) Field of Search ................ 210/87, 192, 199, 210/632, 748; 422/29, 119, 121, 186.3; 250/436

(56) References Cited

U.S. PATENT DOCUMENTS

| 4,204,956 A | * | 5/1980 | Flatow ....................... 210/87 |
| 4,367,410 A | * | 1/1983 | Wood ......................... 250/431 |
| 5,151,252 A | * | 9/1992 | Mass ........................ 422/186.3 |
| 5,624,573 A | * | 4/1997 | Wiesmann ................... 210/748 |
| 6,083,387 A | * | 7/2000 | LeBlanc et al. ............ 210/199 |
| 6,117,335 A | * | 9/2000 | Bender ....................... 210/745 |
| 6,200,466 B1 | * | 3/2001 | Bender ....................... 210/96.1 |

* cited by examiner

Primary Examiner—John R. Lee
Assistant Examiner—Bernard E. Souw
(74) Attorney, Agent, or Firm—Factor & Partners, LLC

(57) ABSTRACT

The invention relates to a UV radiation device for the treatment of fluids, in particular water or waste water. The device includes a radiation chamber through which the fluid can flow in one direction. The radiation chamber essentially comprises a rectangular cross-section and is bordered by two side walls as well as a base wall and a ceiling wall. The side walls and the base wall comprise a non-metallic material. Additionally, a number of lamp units are provided. The lamp units each have a radiation source and a cover tube surrounding the radiation source, and, the lamp units are essentially cylindrical in shape. The lamp units lamp units in at least one cross-direction are arranged towards the flow direction. The distance between two walls diagonally facing each other is less or equal to the discharge length of the radiation source.

14 Claims, 2 Drawing Sheets

UV RADIATION DEVICE FOR TREATING FLUIDS WITH A SIMPLIFIED RADIATION CHAMBER

BACKGROUND OF THE INVENTION

1. Field of the Invention

The present invention relates to UV radiation devices, and in particular to a UV radiation device for treating fluids with a simplified radiation chamber.

2. Background Art

UV radiation devices are known in the art. For example, one UV radiation device is shown in U.S. Pat. No. 4,367,410. There an arrangement, formed from two bulkhead walls and a radiation chamber lying in between which reduces the cross section of the waste water conduit so that the waste water flow to be treated must enter the radiation chamber, is inserted in a gulley of a waste water conduit. A number of lamp units are arranged diagonally to the flow direction in the radiation chamber. The lamp units are in each case arranged above each other in rows in relation to the flow direction. Several rows of lamp units are arranged behind each other in relation to the flow direction.

This known radiation device restricts the cross-section of the waste water conduit which is often undesirable for hydrodynamic reasons. In addition, these devices represent a relatively high technical expense not required by the function of the radiation process itself.

In addition, another radiation device is disclosed in EP 0687201 B1. This reference shows a radiation chamber with radiation sources arranged parallel to the flow direction of the fluid. This configuration is in practice also seen as disadvantageous since the radiation sources with the total lamp unit have to be removed from the conduit for maintenance first in or against the flow direction so that they can be lifted up. In addition, the configuration of lamp units or radiation sources diagonal to the flow direction is advantageous to ensure uniform radiation of the total volume flow.

It is therefore an object of the present invention to create a radiation device with lamp units or radiation sources arranged diagonally to the flow direction which has more favourable hydrodynamic properties and requires much less technical expense.

SUMMARY OF THE INVENTION

In the device disclosed and claimed herein, as at least the side walls and the base wall are made from a non-metallic material and the distance between two walls facing each other in the diagonal direction is less or equal to the discharge length of the radiation source, the total cross section bordered by the non-metallic material (generally concrete) is used as the radiation chamber. Elaborate components which must generally be made as stainless steel parts are no longer necessary. The full cross section formed from the non-metallic material continues into the area in which the radiation sources are arranged, without any hydrodynamically disadvantageous constrictions. Therefore, no unnecessary back pressure is built up in the area of a cross section constriction.

Further, it is possible that the lamp units are held by flange plates which are countersunk providing a seal into recesses of the walls. This preferred form of embodiment enables the conduit and the radiation chamber down to minute recesses to be prefabricated in concrete by construction firms on the spot. The structures necessary for the final installation of the radiation device are limited to relatively small sub-assemblies which reduces both the cost of the radiation device itself as well as the transport and assembly expense necessary.

The lamp units can be held on one side in flange plates, whereby the opposite end can be supported in simply formed recesses. Also, it is possible that the lamp units are held by flange plates facing each other which gives accessibility from both sides and good definition of the fitted position. Uniform and intensive radiation of the fluid flow is possible if rows of lamp units are arranged diagonally at a uniform mutual distance and if several rows are provided behind each other in the flow direction. In this case rows following each other in the flow direction can be aligned cross-wise to each other so that turbulence is deliberately induced in the flow. The distance of the two outer lamp units of a row from the next adjacent wall is preferably smaller or equal to half the distance of two adjacent lamp units from each other. In this way, it is ensured that the radiation intensity directly on the wall is also sufficiently high.

Simple maintenance of the radiation sources is made possible if the cover tube of each individual lamp unit is arranged to provide a seal at least in the flange plate on the connection side and the radiation source is to be fitted and removed without dismantling the cover tube. With such a form of embodiment, radiation sources can be replaced during operation without fluid being able to escape at the connection points between the flange plate and the cover tubes. The radiation chamber during operation is preferably under pressure which ensures high flow speeds within the radiation chamber and that the radiation chamber is filled up to the upper limit. Here, the walls of the radiation chamber can be designed in an especially simple way to resist pressure by at least the side walls, preferably also the ceiling wall and the base wall being supported against each other with tension rods running diagonally through the radiation chamber. These tension rods induce further turbulence uniformly distributed over the total radiation chamber, preventing the formation of continuous steady filaments of flow in areas of lesser intensity. The tension rods are preferably provided over the entire length of the radiation chamber and indeed particularly cross-wise horizontally and vertically.

A further improvement of the turbulence in the radiation chamber is achieved when rows of lamp units are staggered behind each other in the flow direction particularly so that a following lamp unit in each case lies in the centre between two lamp units arranged upstream.

To replace radiation sources during normal operation, it is advantageous if the radiation sources are held in the lamp units with brackets and are supplied via an electric connection, the brackets being only accessible when the electric connection is disconnected from the radiation source. Thus, it is ensured that the radiation source not in operation when it gives off UV radiation harmful for humans can be removed from the cover tube. At the same time, this configuration ensures that an individual radiation source can be safely replaced without having to switch off the other radiation sources of the system.

BRIEF DESCRIPTION OF THE DRAWINGS

In the following an example of embodiment of the present invention is described by way of the drawing. This shows.

BEST MODE FOR PRACTICING THE INVENTION

Figure 1:
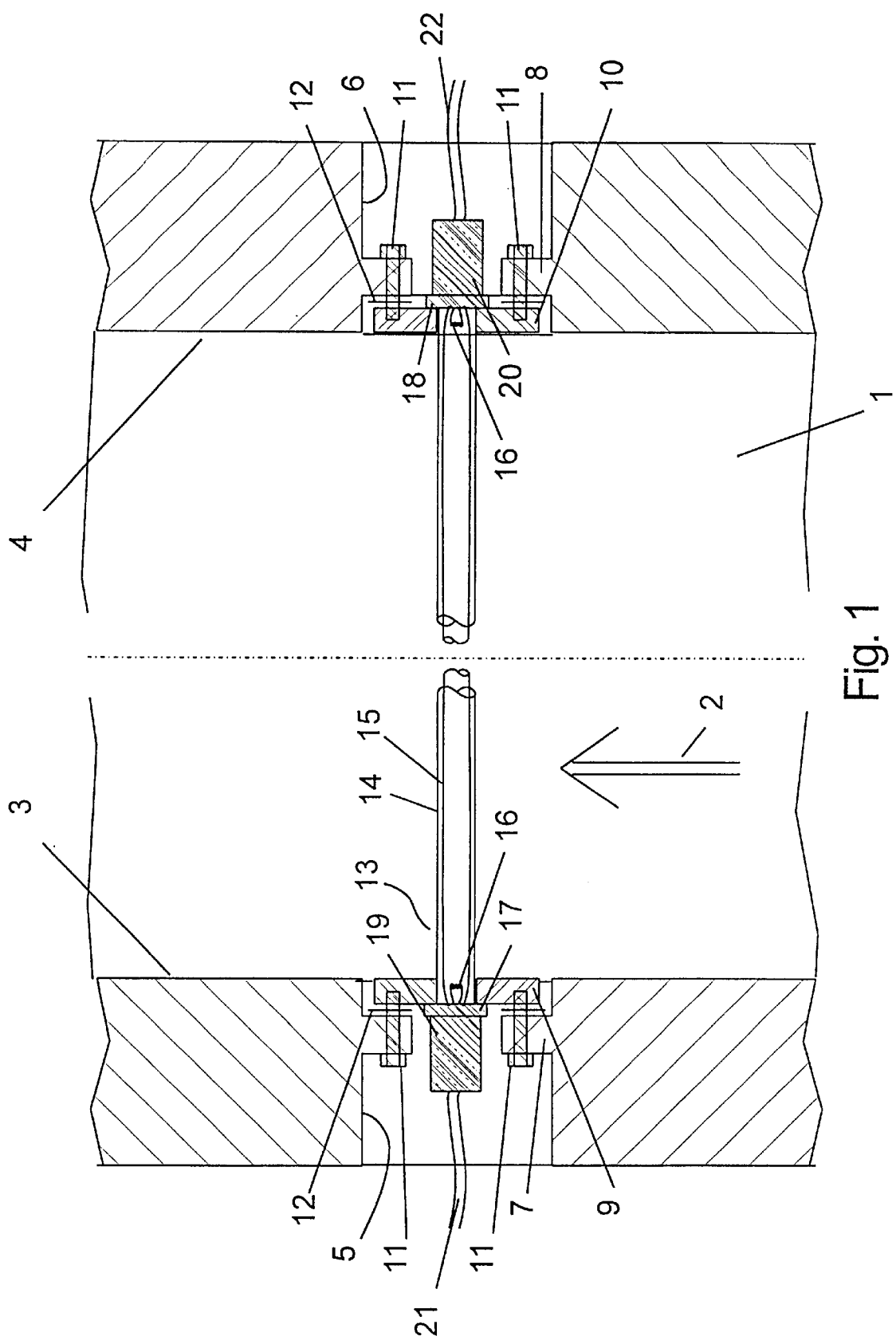
FIG. 1: A radiation device according to the invention as a cross-sectional view taken from above; as well as FIG. 2: Another form of embodiment of a radiation device with one-side accessibility to the lamp units.

While this invention is susceptible of embodiment in many different forms, there is shown in the drawings and will be described in detail, specific embodiments with the understanding that the present disclosure is to be considered as an exemplification of the principles of the invention and is not intended to limit the invention to the embodiments illustrated.

FIG. 1 shows a radiation chamber of a UV radiation device as a cross-sectional view taken from above.

The radiation chamber is bordered on its underneath by a base wall 1 and in relation to a flow direction 2 by a left side wall 3 and a right side wall 4. The side walls 3 and 4 in each case have a recess 5, 6 supporting bridges moulded in one-piece 7, 8 which run in the vertical direction. The bridges 7, 8 hold flange plates 9, 10, inserted from the inside of the radiation chamber which are connected with the side walls 3, 4 by means of threaded screws 11 from the outside with a flexible rubber gasket 12 inserted in between.

The flange plates 9, 10 support between them a lamp unit 13 which, in detail, surrounds a cover tube 14 and a radiation source 15 in the form of a low pressure gas discharge lamp. During operation, a gas discharge producing UV radiation takes place between two helices 16. The connection between the cover tube 14 and the flange plates 9, 10 is liquid-tight and pressure-resistant. A base 17, 18 at each end of the radiation source 15 holds the radiation source 15 in the centre of the cover tube 14. At both ends of the lamp unit 13 in each case, a coupling 19, 20 as well as electric connection wire 21, 22 to supply power to the radiation source 15 is also provided.

Figure 2:
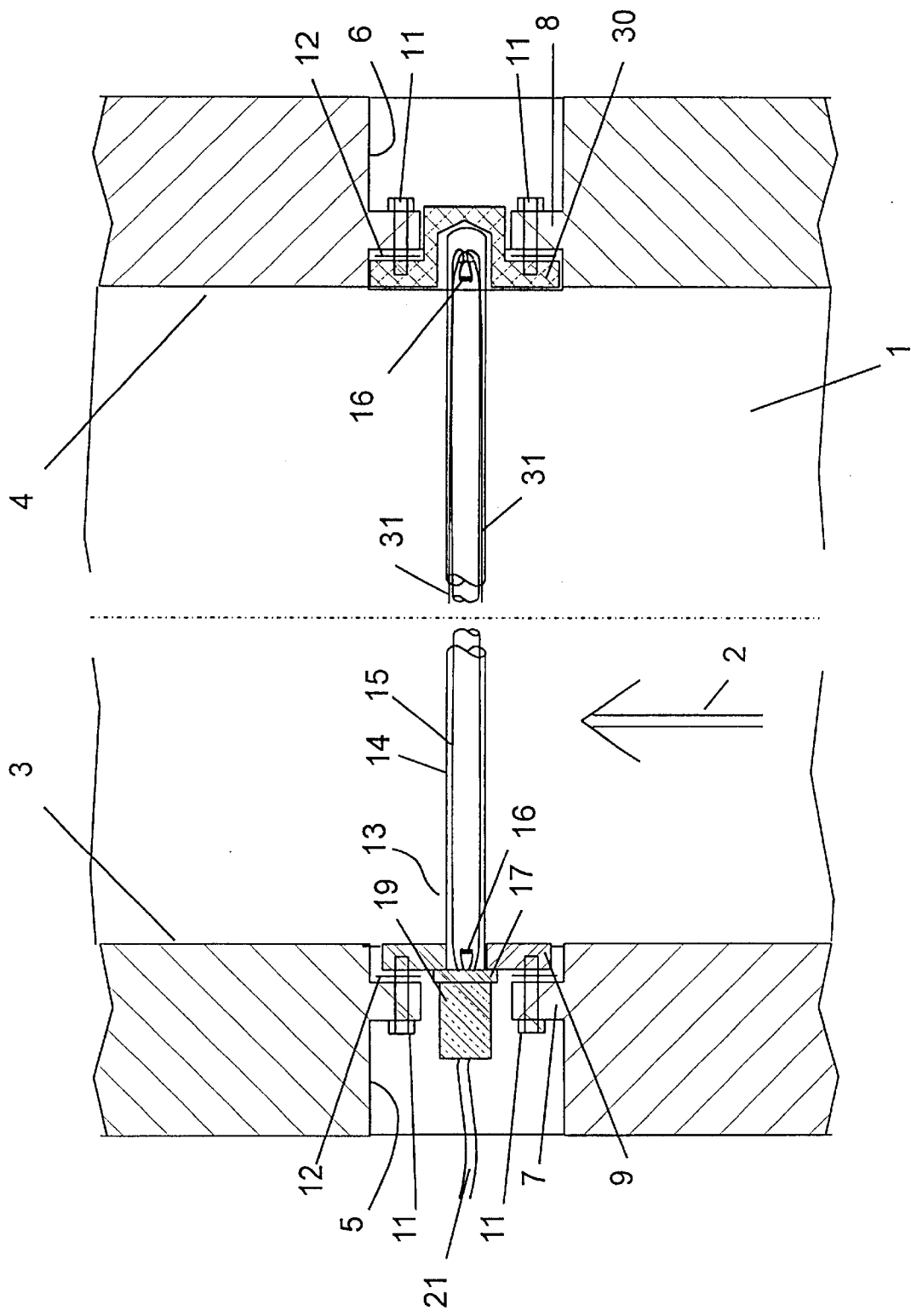

FIG. 2 shows an embodiment wherein the right side wall 4, instead of the flange plate and its bracket to this for the lamp unit 13, supports a bell-shaped bracket 30. The bell-shaped bracket 30 serves to axially and radially fasten the free end of the lamp unit 13 closed here. The electric connections of the radiation source 15 are fed by means of thin electric wires 31 inside the cover tube 14 to the opposite side and are connected to an external power supply unit via the connection wire 21. This particular embodiment is advantageous if easy accessibility of the radiation device is only possible from one side, in the example of embodiment shown from the left side wall 3.

For manufacturing a UV radiation device described in this regard, for example, for potable water, first a concrete gulley is produced which encircles the base wall 1, the side walls 3 and 4 as well as an upper ceiling wall not illustrated. The recesses 5, 6 are provided during construction by the client. Thus, the flange plates 9, 10 or one side the flange plates 9 and facing the bearings 30 with corresponding seals 12 are fitted into the recesses 5, 6. Here, depending on the design of the UV radiation device, flange plates are provided for a number of lamp units 13. The flange plates 9, 10 can be inserted individually for each lamp unit 13. Also, rectangular flange plates with apertures can be provided for a whole row of lamp units 13. Finally, large surface flange plates can be provided which can hold several rows of lamp units 13 behind each other.

The distance of the side walls 3, 4 from each other and the depth of the recess from the surface of the side walls 3, 4 to the bridges is such that on the one hand the flange plates 9, 10 are sealed off flush with the surfaces of the side walls 3, 4 and on the other hand the helices 16 of the radiation sources 15 as far as possible do not lie inside the free inner space. In this way, it is ensured that in the vicinity of the flange plates 9, 10 apart from through the cross-section constriction formed by the lamp units 13 no further cross-section constriction takes place. The "countersunk" position of the helices 16 in the side walls 3, 4 also means that only the fully effective part of the radiation from the radiation sources 15 is applied to the fluid flow. In the vicinity of the helices 16, according to experience, the UV intensity given off by the radiation sources 15 is lower than in the remaining free area. The UV-intensity applied to the total cross-section of the fluid flow 2 is therefore uniform.

To replace the radiation sources 15, in the example of the embodiment according to FIG. 1, on both sides, in each case the holder 19, 20 can be detached and the radiation source 15 can be removed from the cover tube 14 without dismantling the cover tube 14. Here, the total system remains fluid-tight. Since, when detaching the holder 19, 20, the electrical connection to the radiation sources 15 is disconnected, the radiation source 15, after being removed, is also out of operation so that the operatives are not exposed to UV radiation. The other lamps are not switched off in order to replace the radiation source 15, so that the system can remain in operation.

With the form of embodiment according to FIG. 2, replacement of a radiation source 15 is further simplified. Here, only the holder 19 needs to be detached and the radiation source 15 only then needs to be removed from the cover tube 14 on the open side. The new radiation source 15 can be inserted, the holder 19 refitted and finally, the new radiation source 15 can be switched on.

In another embodiment, vertically arranged lamp units 13 which are aligned diagonally to the flow direction 2 can also be provided. Also rows of lamp units can be arranged cross-wise, for example alternatively horizontally and vertically. In the case of concrete gullies subjected to relatively high pressure, it is possible that the side walls 3, 4 are supported against each other with tension rods which run diagonally through the radiation chamber and for example are aligned parallel to the lamp units 13. These tension rods, apart from improved compressive strength, also ensure good turbulence of the fluid flow, so that uniform radiation of all the particles contained in the fluid is assured. Also, the tension rods can be aligned vertically or cross-wise to support the base and ceiling wall. With the tension rods described even in the case of relatively thin-walled concrete gullies, depending on the particular design, good compressive strength is achieved.

A considerable advantage of the device described in this respect consists in the fact that nearly the total radiation chamber, down to the structural elements connected with the flange plates 9, 110, can be prefabricated in concrete or other non-metallic material relatively economically and the relatively expensive corrosion-resistant components which are normally made from stainless steel can be reduced to a minimum. As a result, considerable simplification is achieved especially in the construction of new waste water or potable water radiation systems.

The dimensioning of the corresponding devices is known from prior art, especially, in order to achieve the intended radiation dose to disinfect waste water or potable water. The lamp units preferably comprise a discharge length of at least 800 mm (for instance corresponding to the distance between the side walls 3 and 4). Longer UV radiation sources with discharge lengths of 1.20 m or even 1.60 m are preferred. The modules preferably in this case have a diameter of more than 30 mm. The distance of the UV modules within a row should be selected so that water layer thicknesses are at least 60 mm. The radiation chamber here has a clear cross-section of at least 0.6 m².

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A UV radiation device for the treatment of fluids, in particular water or waste water, comprising:

a radiation chamber through which the fluid can flow in one direction, the radiation chamber including two side walls as well as a base wall and a ceiling wall, at least the side walls and the base wall comprising a non-metallic material;

a plurality of lamp units, each comprising a radiation source, a cover tube surrounding the radiation source and a discharge length, each lamp unit is arranged relative to the radiation chamber so as to be in the cross-direction of the flow direction, wherein the distance between the two walls diagonally facing each other is less than or equal to the discharge length of the radiation source.

2. The UV radiation device according to claim 1, further comprising:

at least one pair of flange plates countersunk into corresponding recesses of the side walls, the at least one pair of flange plates capable of retaining a lamp unit therebetween.

3. The UV radiation device according to claim 2, wherein the flange plates face each other.

4. The UV radiation device according to claim 1, wherein the plurality of lamp units are substantially positioned diagonally and in a substantially equally spaced apart orientation in the flow direction.

5. The UV radiation device according to claim 1, wherein the plurality of lamp units are substantially aligned in a cross-wise orientation relative to each other.

6. The UV radiation device according to claim 1, wherein the distance between two outer lamp units of a row from the next adjacent wall is less or equal to half the distance of two adjacent lamp units from each other.

7. The UV radiation device according to one claim 1, wherein the cover tube of each lamp unit is arranged providing a seal at least in a flange plate on a connection side thereof, to in turn, facilitate the fitting and removal of the radiation source without the dismantling of the cover tube.

8. The UV radiation device according to claim 1, wherein the radiation chamber is under pressure during operation.

9. The UV radiation device according to claim 1, further comprising a plurality of tension rods, the tension rods being positioned diagonally through the radiation chamber and affixed to the side walls.

10. The UV radiation device according to claim 9, wherein the tension rods are further affixed to at least one of the base wall and ceiling wall.

11. The UV radiation device according to claim 9, wherein the plurality of tension rods are provided over the total length of the radiation chamber.

12. The UV radiation device according to claim 10, wherein the tension rods are arranged both horizontally and vertically, in a cross-wise orientation.

13. The UV radiation device according to claim 1, wherein the lamp units are aranged in rows behind each other and staggered against each other in the direction of flow.

14. The UV radiation device according to claim 1 wherein the radiation source is attached by brackets in the lamp units and power is supplied thereto via an electric connection, wherein the electrical connection precludes access to the brackets unless disconnected from the radiation source.

* * * * *